United States Patent [19]
Fujii et al.

[11] Patent Number: 5,240,006
[45] Date of Patent: Aug. 31, 1993

[54] APPARATUS FOR DISPLAYING A BLOODSTREAM STATE

[75] Inventors: Hitoshi Fujii, Fukuoka; Hideo Tomoda, Tokyo; Takashi Yokokura, Tokyo; Masaru Satoh, Tokyo, all of Japan

[73] Assignees: Hitoshi Fujii, Fukuoka; Kabushiki Kaisha Topcon, Tokyo, both of Japan

[21] Appl. No.: 704,431

[22] Filed: May 23, 1991

[30] Foreign Application Priority Data

May 24, 1990 [JP] Japan .................. 2-134860

[51] Int. Cl.⁵ .................. A61B 5/0265; A61B 3/10
[52] U.S. Cl. .................. 128/665; 128/691; 128/687; 351/221
[58] Field of Search ............ 128/633, 664, 687, 676, 128/688, 689, 691, 665–667; 351/221

[56] References Cited

U.S. PATENT DOCUMENTS

| | | | |
|---|---|---|---|
| 4,877,322 | 10/1989 | Hill | 351/221 |
| 5,042,939 | 8/1991 | Zayek | 351/206 |
| 5,090,799 | 2/1992 | Mikano et al. | 351/221 |
| 5,106,184 | 4/1992 | Milbocker | 351/221 |

Primary Examiner—Lee S. Cohen
Assistant Examiner—Kevin Pontius
Attorney, Agent, or Firm—Finnegan, Henderson, Farabow, Garrett & Dunner

[57] ABSTRACT

An apparatus for imaging and displaying a blood stream state of an eye to be tested. A laser beam is first irradiated onto an eye to be tested. And light reflected from an irradiated area on the eye is detected and information about the reflected light is stored. And second, the bloodstream state of the eye are calculated on the basis of the information, the imaged results are displayed on a display means of the apparatus. At the same time, a pulse wave of a person to be tested is detected by a pulse wave detecting means, the wave shaped of the pulse wave is displayed by a display controlling means, which controls to display the measuring time and portion of the bloodstream state compositely on the present wave shape.

5 Claims, 5 Drawing Sheets

APPARATUS FOR DISPLAYING A BLOODSTREAM STATE

BACKGROUND OF THE INVENTION

1. Field of the Invention

This invention relates to an apparatus for two-dimensionally imaging and displaying a bloodstream state of a retina, an iris and so forth by measurement of a laser beam and consideration of a change of the bloodstream based on a change of a pulse wave.

2. Description of the Prior Art

One of well-known conventional methods for observing a bloodstream state of an eye is a method by Doppler effect of a laser beam reflected from a retina, and another by photographing of speck patterns of the reflected laser beam.

An apparatus for imaging and displaying the bloodstream state is recently being improved in the cause of advantages as follows:

It permits of a direct observation of a bloodstream state in a blood vessel without injuring an eye to be tested. Since a state of an obstruction in the blood vessel can be observed by information of the speed of bloodstream, the bloodstream states before and after an operation for diabetic retinitis with the optical coagulation can be compared in detail, so that an infallible cure is taken.

It is effective in diagnosis of adult diseases such as high blood pressure or arteriosclerosis on the analogy of a state of an eye thereby.

It is effective in diagnosis of a circulatory disease of an aortic syndrome, a brain circulatory disease and so forth.

BRIEF SUMMARY OF THE INVENTION

A human pulse rate is usually 60 to 120 per minutes (or 1 to 2 per second), and the shortest period of the pulse wave has at least 500 milliseconds. Therefore, when the state of the bloodstream of an iris or a retina, for example, are imaged and displayed, the speed of bloodstream on the wave peaks is relatively higher than that upon the wave trough in the case of measurement upon the peak of the pulse wave; conversely the speed upon the trough is relatively lower than that upon the peak in the case of measurement upon the trough. And accordingly, measurement without due consideration for a change of the pulse wave results in the unreliability.

The average speed of bloodstream may be obtained by measurement during a period from the peak to the next peak of a pulse wave (or during one cycle). An an eye to be tested must be in a fixed stare at least for one minute so as to maintain the accurate measurement of the bloodstream at the same height on the pulse wave when measured. It is, however, difficult owing to continuous slightest tremors of an eye. Furthermore, the operation is complicated and requires a skilled operator.

An object of the invention is to provide an apparatus for imaging a bloodstream state capable of gaining most reliable measured results of a bloodstream state of an eye to be tested, considering a change of the pulse wave in the meantime. To accomplish it, the apparatus comprises pulse wave detecting means for displaying a pulse wave of a person to be tested, display means for displaying the pulse wave together with the imaged bloodstream state on the display means for displaying a bloodstream state of an eye to be tested, and display controlling means for making the display means display measuring time and portion compositely on the pulse wave.

In an apparatus for displaying a bloodstream state according to the invention, a laser beam is irradiated onto an eye to be tested and light reflected from the irradiated area on the eye is detected and information about the reflected light is stored. The bloodstream state of the eye is calculated on the basis of the stored information, the imaged calculations are displayed on display means. At the same time, a pulse wave of a person to be tested is detected by pulse wave detecting means. The wave shape of the pulse wave is displayed by display controlling means which controls to display the measuring time and portion of the eye compositely on the present wave shape.

DETAILED DESCRIPTION OF PREFERRED EMBODIMENTS

Reference will now be made in detail to the presently preferred embodiment of the invention as illustrated in the accompanying drawings.

Figure 1:
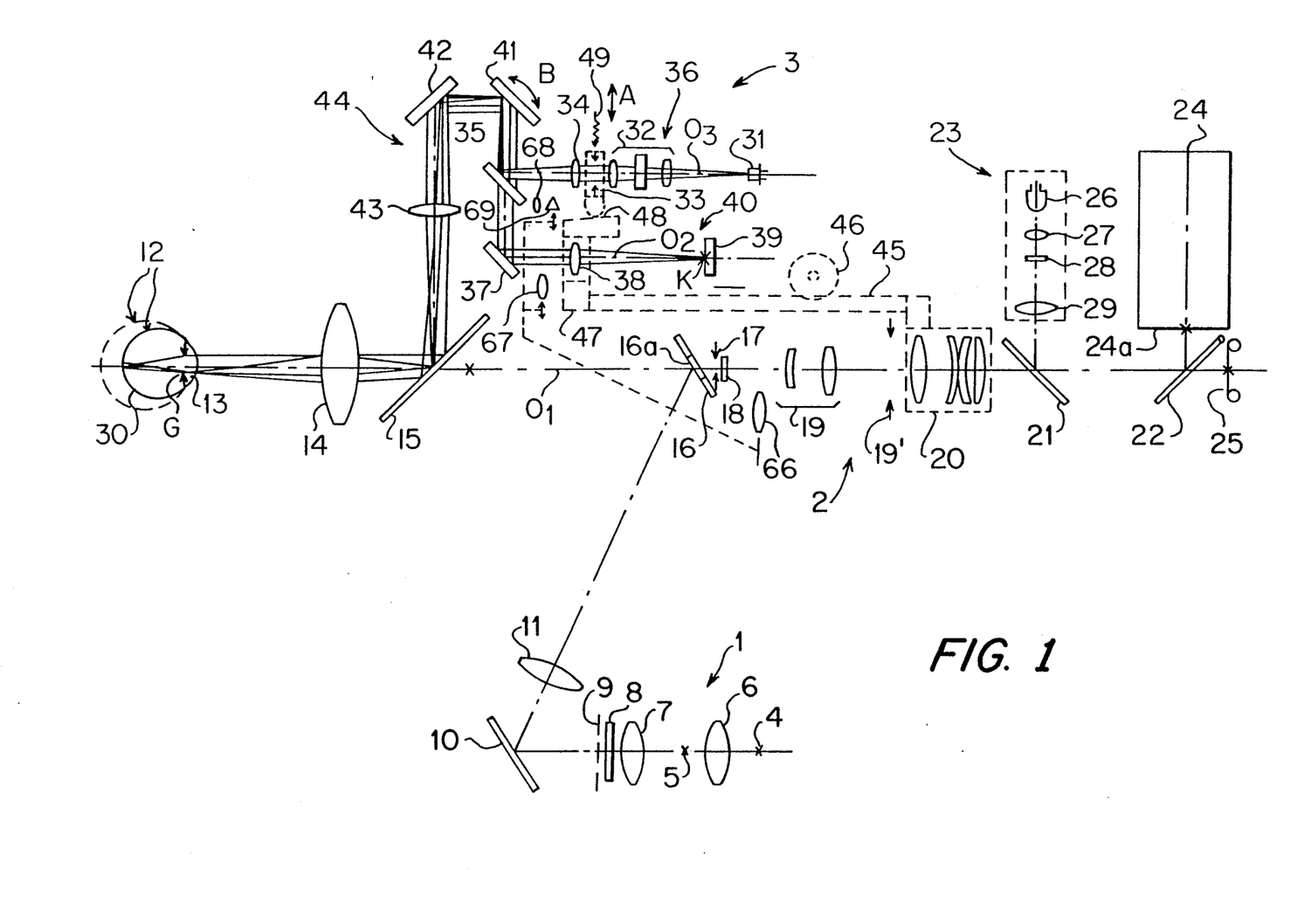
FIG. 1 shows an optical system of an apparatus for imaging a bloodstream state according to the invention.

Referring to FIG. 1, the reference numbers 1, 2, 3 designate an illuminating system for observation and photographing, an optical system for observation and photographing, and an optical system for measurement, respectively.

The illuminating system for observation and photographing 1 includes an illuminating source for observation 4, an illuminating source for photographing 5, condenser lenses 6, 7, an infrared raysimpermeable and visible rays-permeable filter 8, a ring slit 9, an oblique mirror 10, and a relay lens 11. The sources 4 and 5 are conjugate with the condenser lens 6, and the ring slit 9 is approximately conjugate with a pupil 13 of an eye to be tested.

The optical system for observation and photographing 2 includes an objective lens 14, a dichroic mirror 15, a perforated mirror 16, a diaphragm 17, an auxiliary lens 18 for compensating refractive indexes, a relay lens 19, a diaphragm 19−, a condenser lens 20, a half mirror 21, a quick return mirror 22, a reticule projecting optical system 23, a TV camera 24, and a film 25.

The dichroic mirror 15 reflects only a laser beam of wavelength 830 nm and permeates illuminating visible rays. A light-receiving surface 24a of the TV camera 24 and the film 25 are conjugate with the quick return mirror 22. The mirror 22 is dislocated out of the optical path of the illuminating system for observation and photographing when photographed. The reticule projecting optical system 23 includes an illuminating source 26, a condenser lens 27, a reticule plate 28, and an image-forming lens 29. A reticule image of the reticule projecting optical system 23 can be received into the TV camera 24 through the half mirror 21 and the quick return mirror 22, and it can be imaged on the film 25.

The reticule image is composed of cross-hairs and rectangular-like frame. The size of the frame is decided so as to take the same almost as CCD described hereinafter.

The source for observation 4 is turned on to observe a retina 30, The illuminating light passes through the oblique mirror 10, the relay lens 11, the perforated mirror 16, the dichroic mirror 15, and the objective lens 14, and finally reaches the eye to be tested. The light converted into a ring-circular luminous flux in the vicinity of the pupil 13 illuminates the retina 30. The reflected light from the retina is emitted from the eye 12 and then reaches the dichroic mirror 15 via the objective lens 14. After permeating the mirro 15, it passes through the hole 16a of the perforated mirror 16. It is imaged on the image-receiving plate 24a of the TV camera 24 by the action of the relay lens 19 and the condenser lens 20. The camera 24 is used to observe an image of the retina. The auxiliary lens 18 is inserted into the optical path of the optical system for observation and photographing 2 in the case of too high refractive power of the eye 12 and the difficulty of the focusing upon the retina 30 therefor.

The optical system for measurement 3 comprises a laser beam projecting optical system 36 for projecting a laser beam to the retina 30 or the front of the eye, the system 36 having a laser diode 31, a lens system for transforming a laser beam 32, a diaphragm member 33, a lens 34, and a half mirror 35, a detecting optical system 40 for detecting the reflected light from the retina 30 or the front of the eye (an iris and sclera), the system 40 having a reflecting mirror 37, an image-forming lens 38, and CCD 39, and a common optical system 44 having a movable mirror 41 for changing the angle of the flux of light, a reflecting mirror 42, and a lens 43.

A small and quickly starting-up and finishing-off TTL driving type is more advantageously used to cut off the light flux from the laser diode 31 than a shutter. The wavelength of the laser beam of the diode 31 is near infrared rays (830 nm in the embodiment) so as to prevent a pupil from being shrunken, and the diode 31 is a single mode in order to obtain a good contrastive speckle pattern on CCD 39. The diode 31 is driven by a drive circuit of a controlling means described hereinafter, which controls temperature in order to restrain the fluctuation of the wavelength of the laser beam and the output fluctuation within the duration of the bloodstream measurement, the controlling means comprising a well-known thermistor and a Peltier element.

The laser beam transformation lens system 32 made of the combination of a cylindrical lens and a spherical lens transforms an ellipitic laser beam into an approximately circular beam in a cross section thereof. The irradiation efficiency of the laser diode 31 is enhanced by the transformation. An anamorphic prism may be used for the transformation in place of the cylindrical lens. The diaphragm member 33 works for defining an irradiation field. The member 33 is driven in the arrow A direction by a cam member described hereinafter.

The lens 34 converges the laser beam upon the movable mirror 41. The mirror 41 rotates in the arrow B direction and also moves in the direction perpendicular to the drawing sheet. The mirror 41 is approximately conjugate with the pupil 13. In detail, the laser beam of light of the laser diode 31 is reflected by the movable mirror 41 and then an image G of the beam is formed in the vicinity of the pupil 13 as shown enlargedly in FIG. 2. The diaphragm member 33 is approximately conjugate with the retina 30. An image 33 of the member 33 is formed upon the retina 30. The member 33 has a square-shaped opening portion corresponding to the size of CCD, being used for irradiation of a laser beam of the quantity of light required to measure the bloodstream of the retina 30 thereupon. The center $K^-$ of the image 33 corresponds to the center K of CCD 39 on the retina. For example, the rotation of the movable mirror 41 in the arrow B direction brings about a dislocation of the position of the image $33^-$ on the retina 30 because of occurrence of the inclination of light for forming the image G with the position of the image G unchanged. Accordingly, the movable mirror 41 acts as selection of the area of the retina to be measured. The reticule plate 28 for showing the area for irradiation is constituted so as to move twodimensionally on the surface perpendicular to the optical axis corresponding to the motion of the movable mirror 41. Namely, the determination of an irradiation area based on the plate 28 permits to measure it. Movement of the reticule projecting optical system 23 may be conducted in place of the plate 28.

The condenser lens 20 is moved back and forth along the optical axis 01 for observation and photographing by a driving mechanism comprising a rack 45 and a pinion 46. A holding member 47 for holding an image-forming lens 38 is connected to the rack 45 and is moved back and forth in the direction of an optical axis 01 of the detecting optical system 40, being corresponding with the condenser lens 20. The member 47 is constituted of the cam 48. The diaphragm member 33 is driven in the arrow A direction (as described hereinbefore) perpendicular to an optical axis of the laser beam projecting optical system 36, corresponding to the movement back and forth of the image-forming lens 30. The number 49 designates a spring for perpetual contact of the diaphragm member 33 with the cam face 48.

Figure 2:
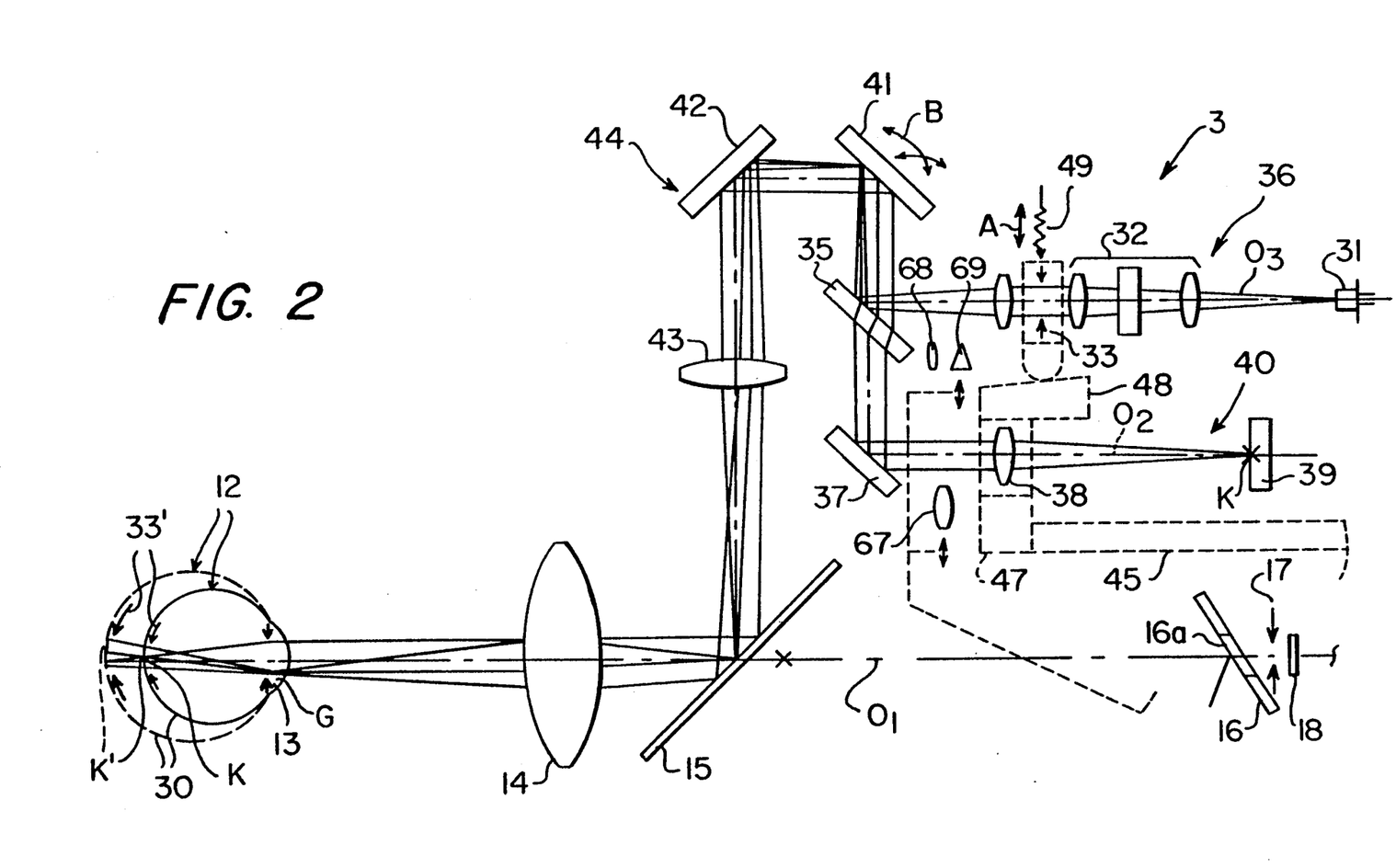
FIG. 2 shows a partially enlarged view of FIG. 1.

The reason for the drive of the diaphragm member 33 in the arrow A direction according to the motion of the condenser lens 20 will be explained as follows:

In the case of the different refractive power of the eye to be tested, the center K of CCD 39 and the center K' of the image 33' of the diaphragm 33 formed in the retina 30 are off-set as shown enlargedly in FIG. 2. The stitch line 12 in FIG. 2 designates an eye to be tested whose volume is different from that of the eye 12 shown with the continuous line. The continuous line shows an actual volume of the eyeball. And the eyeball shown with the stitch line is optically equivalent to the eye having a different refractive power from the eye with the continuous line. When the diaphragm 33 is driven in the arrow A direction, the center K' of the image 33' on the retina 30 shown with the stitch line is moved so as to be superimposed on the center K of CCD 39 with the position of the image G on the pupil 13 unchanged. The position of the image 33' on the retina 30 and the irrdiation area of the eye are changed by the rotation of the movable mirror 41, leaving the area of the center K' of the image 33' and the center K of CCD 39 superimposed.

After the light reflected from the retina changes into a parallel flux of light, it is emitted and reaches the dichroic mirror 15 through the objective lens 14. Then part of the parallel flux advances toward the TV camera 24 and the film 25 through the mirror 15. This advancement permits to observe the image of the retina. A source for photographing 5 is turned on for recording the image of the retina in the film 25 as well as the irradiation area of the retina. Since the image of the reticule plate 28 is also recorded in the film 25 at the same time, the irradiation area on the retina 30 can be recorded.

The remaining parallel flux of light reflected from the irradiation area on the retina is reflected by the dichroic mirror 15, and the flux goes through the lens 43, the reflecting mirror 42, the movable mirror 41, the half mirror 35, and the reflecting mirror 37. It reaches the image-forming lens 38, whereby an retina image is formed on CCD 39. A laser speckle pattern image is also imaged there together with the retina image. In order to enhance the detection sensitivity of the speckle pattern, a pixel size S of CCD 39 is preferably selected as follows:

$$\delta R \leq S \leq 3\delta R$$
$$\delta R = 1.22 \lambda (LO+D)/d$$

where $\delta R$ is an average size of a laser speckle, $\delta$ is a wavelength of a laser beam, LO is a focal length of an image-forming lens 38, d is an effective diameter of the lens 38, and D is an offset amount of focusing.

The laser beam projecting optical system 36 and the detecting optical system 40 are coaxial through the aid of the half mirror 35.

Figure 3:
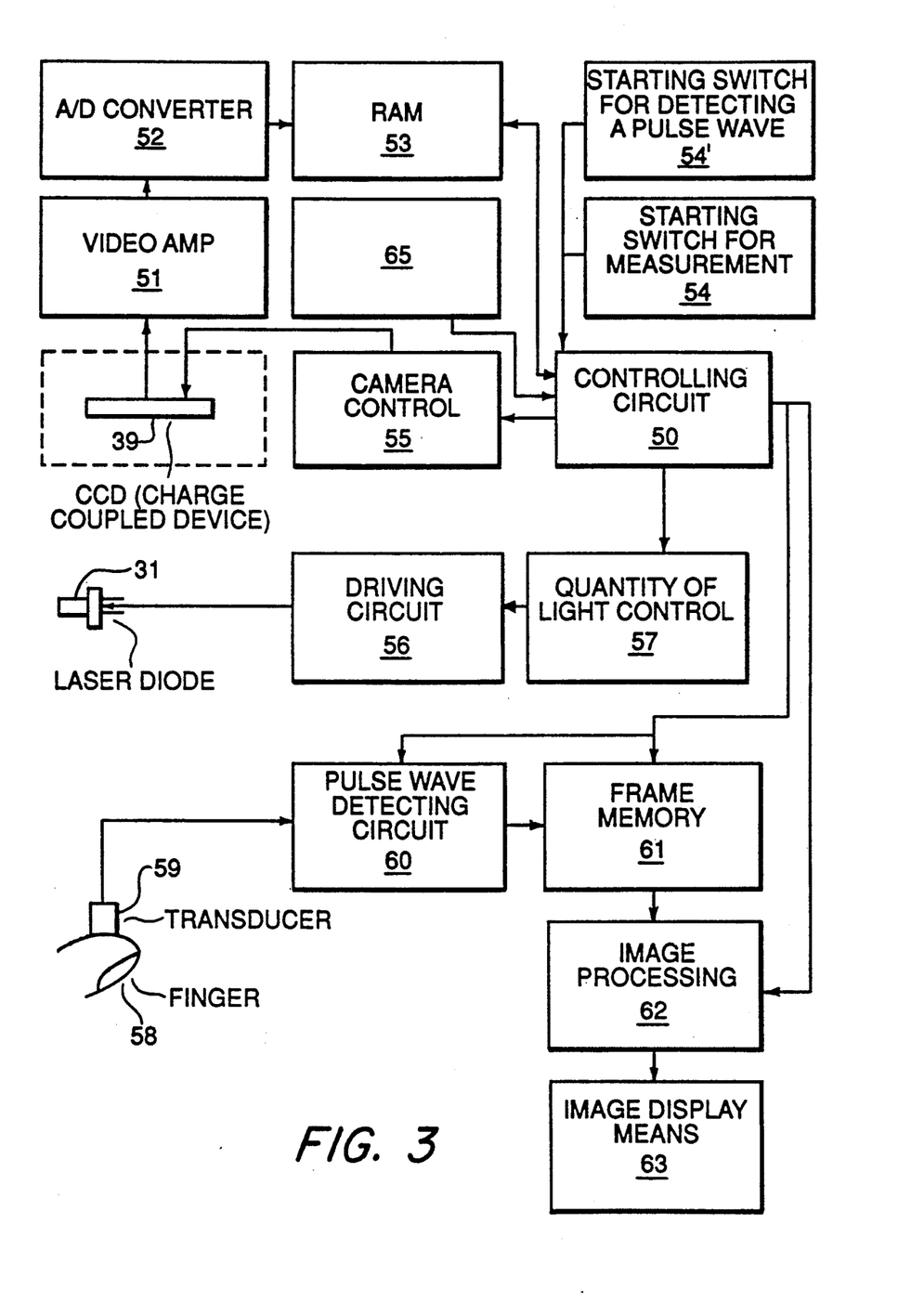
FIG. 3 shows a block diagram of a controlling section of an apparatus according to the invention.

The information signal of CCD 39 based on the laser speckle pattern is output by a controlling circuit 50 of a controlling means in FIG. 3 every one pixel. The output stored in RAK (Random Access Memory) 53 through a video amplifier 51 amd A/D converter 52. Laser speckle patterns for 100 frames, for example, are stored in RAM 53. The circuit 50 makes a camera controlling circuit 55 start scanning CCD 39 by switching on a measurement-starting switch 54, and at the same time it start calculating based on the speckle patterns stored in RAM 53.

In the operation expression, the difference of the two scanning outputs next to every pixel is found by turns. Namely, $$I(m,n) \approx \sum_{K=1}^{N} \frac{|I_{K+1}(m,n) - I_K(m,n)|}{I_{K+1}(m,n) + I_K(m,n)}$$

where I(m,n) is the output of the (m,n)th pictures element, and N is preferably more than 100.

It is possible not only to remove an effect of an continuous slightest tremors of an eye but also a reduce the effect in spite of a great motion of the eye during a detecting time. Each reason for an absolute value of the numerator and a non-absolute value of the denominator in the above expression is based on the measurement of the variable amount itself, and normalization, respectively. Accordingly, an output for a retina image is not produced, and the variable conditions of a speckle signal caused by the speed of bloodstream are pick up or revealed.

The laser diode 31 is controlled by the controlling circuit 50 through a quantity of light controlling circuit 57. The circuit 57 controls a signal-output gained by CCD before measuring the bloodstream, so that the signal-output becomes proper. A transducer 59 is put on a finger 58 of a person to be tested. The output of the transducer 59 is input in the pulse wave detecting circuit 60. The controlling circuit 50 makes the pulse wave detecting circuit 60 drive by switching-on of the starting switch 54⁻ for detecting the pulse wave. The output of the circuit 60 is input in the frame memory 61. The output of the frame memory 61 is input in an image processing circuit 62. The circuit 62 is connected to an image displaying means 63.

Figure 5:
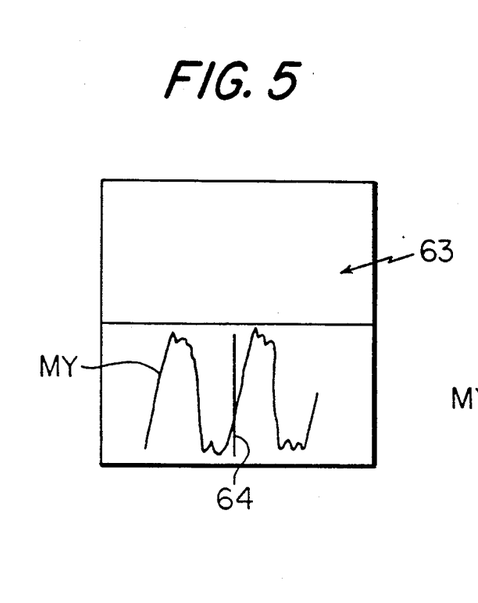
FIG. 5 through FIG. 8 show images on image-display means according to the invention.

The controlling circuit 50 controls the frame memory 61 and the image processing circuit 62 in addition to the pulse wave detecting circuit 60. After switching on the pulse wave detecting starting switch, the wave shape of the pulse wave detected by the pulse wave detecting circuit 60 is displayed on the image displaying means 63 through the frame memory 61 and the image processing circuit 62. As shown in FIG. 5, any portion of the wave shape MY (between the peak and the next peak) for measuring the bloodstream is predetermined by the movement of the linear cursor 64 with the mouse 65.

The measurement of the bloodstream of the retina will be hereinafter described with reference to the flow-chart in FIG. 4.

Figure 4:
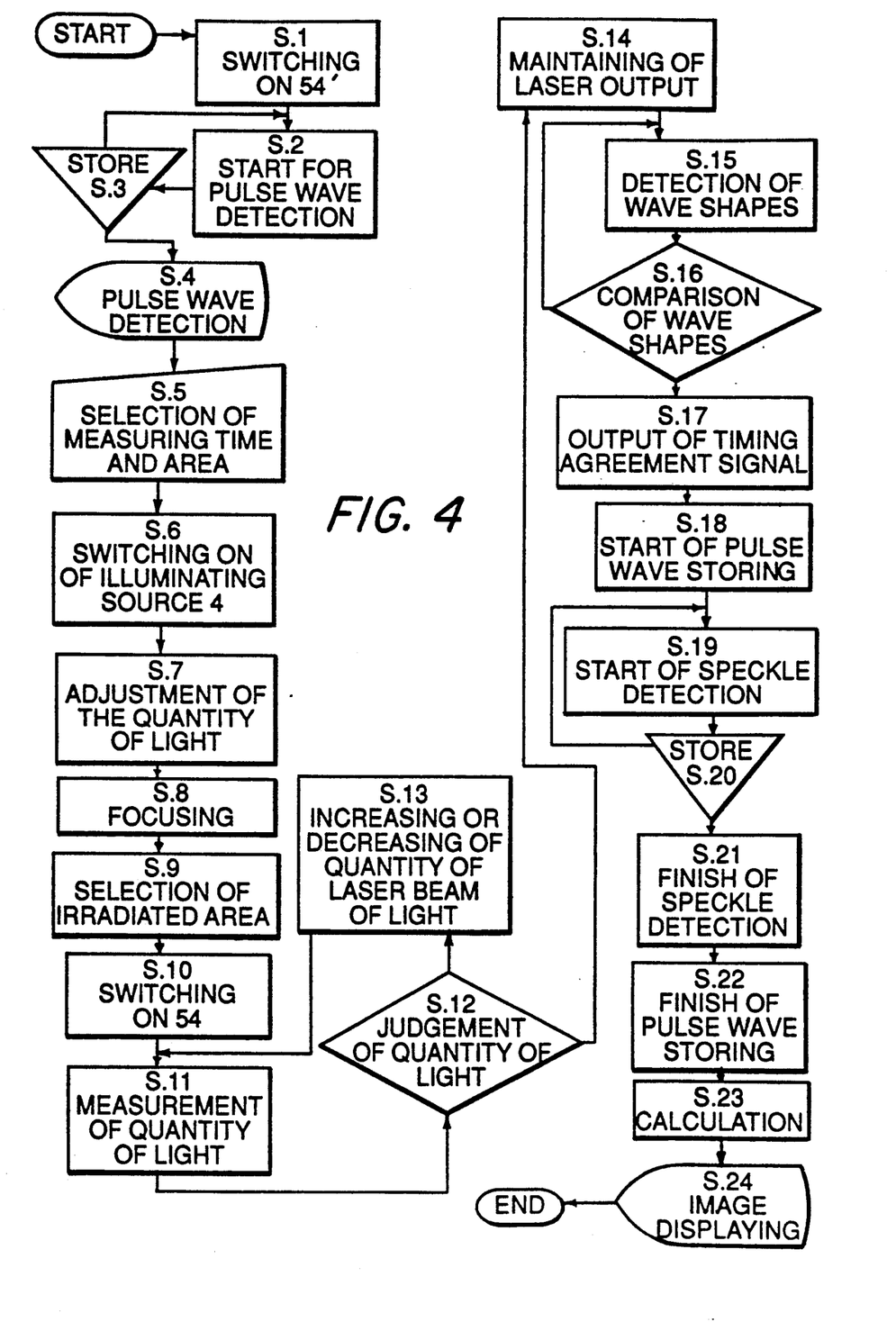
FIG. 4 shows a flow diagram illustrating consecutive processes of an apparatus according to the invention.
Figure 6:
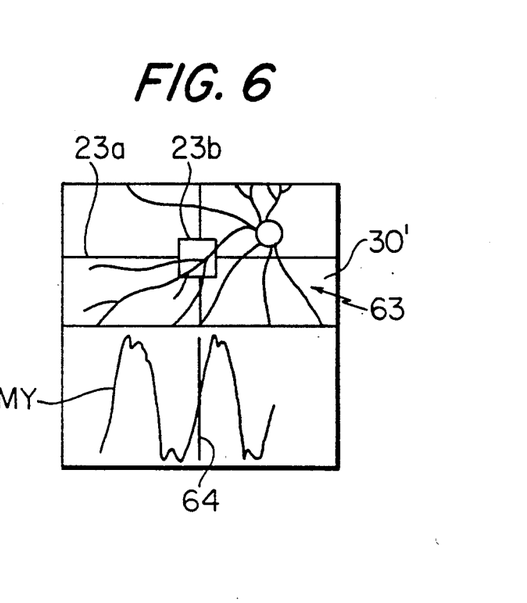

Referring now to FIG. 4, on switching on the pulse wave detecting starting switch 54⁻ (S.1), the detection of the pulse wave starts (S.2) and then information about the pulse wave shape MY is stored in the frame memory 61 at predetermined timing (S.3). The pulse wave shape MY is displayed on the image displaying means 63 as shown in FIG. 5 (S.4). Next, a level of the wave shape MY for the measurement is predetermined by the linear cursor 64 with the mouse 65 (S.5). The illuminating source for observation 4 is turned on (S.6). An image 30⁻ of the retina 30 is displayed on the image-displaying means 63 as shown in FIG. 6. At the same time, cross hairs 23a and a frame 23b of the cross hairs are displayed compositely on the image 30⁻.

The the quantity of illuminating light for observation is adjusted by a quantity of light adjusting means (not shown) (S.7). After the optical system for observation and photographing 2 is focused upon the retina 30 (S. 8), the illuminated area on the eye to be tested (on the retina in the embodiment) is selected by the adjustment of the movable mirror 41 (S. 9). After the preparations for measurement (Step 1 through Step 9), the measuring starting switch 54 is switched on (S. 10). The laser diode 31 is driven and the laser beam of light is irradiated upon the retina 30. CCD 39 receives the laser beam of light reflected from the retina 30. The quantity of light is measured on the basis of all the quantity of received light by CCD 39 (S. 11). The measurement is made by the controlling circuit 50. The circuit 50 judges the quantity of reflected light (S. 12). In detail about the judgment, the quantity of light of the laser diode 31 is increased or decreased in the case of the quantity beyond the predetermined limits. The circuit 50 repeats Steps 11 through 13 until all the quantity of received light on CCD 39 gains that within the predetermined limits. The output from the laser diode 31 is kept constant under the state of the quantity of light on CCD 39 within the predetermined limits (S. 14).

Figure 7:
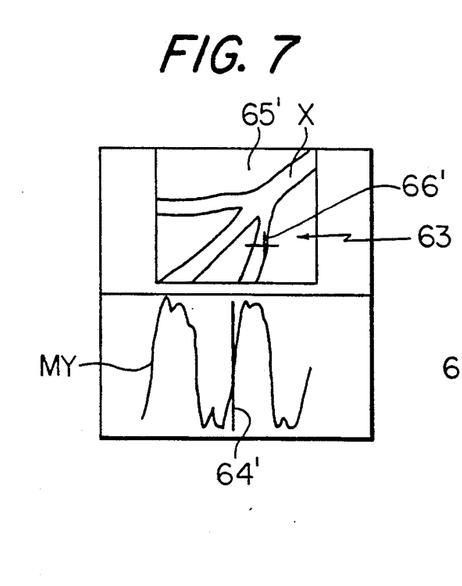

The controlling circuit 50 detects the wave shape MY of the present pulse wave before and after measuring the bloodstream (S. 15), and it judges whether or not the level of the present wave shape MY agrees with that of the predetermined wave shape MY (S, 16). The steps 15 and 16 are repeated in the case of disagreement of the two levels within the predetermined limits. A timing agreement signal is output in the case of agreement within the predetermined limits (S, 17). Based on the output, the information about the wave shaped MY immediately before measurement of the bloodstream are stored in the frame memory 61 (S. 18). Next, a laser speckle for measurement of the bloodstream with CCD 39 is detected (S. 19) and data about each pixel of the laser speckle are stored in the frame memory (S. 20). At the same time as the completion of the store, the detection of the speckle ends (S. 21). There ends the store of the information about the wave shape MY immediately after measurement of the bloodstream in the memory 61 (S. 22). The controlling circuit 50 calculates based on the data concerning the laser speckles stored in the frame memory 61 (S. 23). The image processing is carried out on the basis of the calculations. At the same time, there is carried out an image processing for the wave shape MY stored in the frame memory 61 before and after the measurement. These wave shaped are displayed on an image displaying means 63 as shown in FIG. 7 (S. 24). The reference number 64⁻ designates a linear cursor compositely displayed on the wave shape MY before and after measurement of the bloodstream. The reference number 65⁻ designates the calculations imaged in mosaic. The reference character X designates blood vessels of the retina 30. In this embodiment, the speed of the bloodstream of the retina 30 is displayed gradually coloredly in accordance with the speed such as red to the quickest bloodstream and blue to the slowest. Therefore, it is possible to judge the level of the wave shape MY of the measurement carried out. The controlling circuit 50 is a display controlling means, which display the wave shape together with the imaged calculations, and at the same time allow to display the linear cursor 64⁻ showing the measuring time and area compositely on the wave shape MY.

Figure 8:
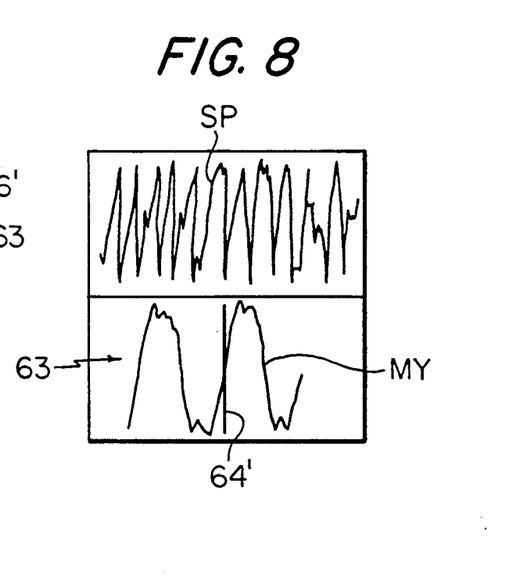

The speckle signal SP of the pixel assigned by the image displaying means 63 is displayed as shown in FIG. 8 when one pixel of CCD 39 is assigned by the cross cursor 66⁻ with the mouse 65. An observation of the speckle signal SP permits of a detailed diagnosis.

The measurement of the bloodstream conditions of an iris at the front portion of an eye to be tested requires an illumination by a front portion-illuminating source (not shown) to the front.

Auxiliary lenses for focusing 66, 67, 68 are inserted in the optical system for observation and photographing 2, the optical system for detection 40, and the laser beam projecting optical system 36. Furthermore, a prism 69 is inserted into the optical system 36. The auxiliary lens 66 works for focusing an image of the front portion upon the TV camera 24, and the film 25. The auxiliary lens 66 works for moving an image 33⁻ of the diaphragm member 33 to the vicinity of the pupil 13. In detail, the insertion of the auxiliary lens 68 into the optical system 36 brings about the movement of an image G of the laser diode 31 conjugate with the pupil 13 to the front of the eye 12. Accordingly, the image 33⁻ of the diaphragm member 33 is formed in the vicinity of the pupil 13. The prism 69 works for agreement of the center K of CCD with the center K⁻ of the image 33⁻ on the pupil 13. The rotation of the movable mirror 41 permits of the selection of the irradiation area on the pupil 13 with the centers K⁻ and K agreed. The auxiliary lens 67 works for focusing an image of the front portion of the eye upon CCD 39. The details of the process for measuring the bloodstream conditions concerning the front will be omitted because of the approximately same process concerning the retina.

The invention is not limited to the specific details shown and described, it furthermore includes the followings:

A correction of a refractive index of an eye to be tested can be carried out by a simultaneous drive of the lens system 32 for transforming a laser beam and the laser diode 31 in a direction along the optical axis 03.

A correction of a refractive index of an eye to be tested can be carried out by a movement of a diaphragm member 33 in connection with the condenser lens 20 in a direction along the optical axis 03.

It is possible to confirm an image of the retina 30+ by using only CCD 39 without a TV camera. In the case, the configuration of such a circuit as the scanning limits of CCD 39 are assigned permits to take out the speckle signal SP within the predetermined detecting limits.

The configuration of projection of a reticule image showing an irradiation area onto a finder system for observation permits to measure the bloodstream by observation of an image of the retina through a finder.

What is claimed is:

1. An apparatus for imaging and displaying the velocity of blood in a vessel, said apparatus comprising:
   means for directing a laser beam toward an eye of a person to be tested to obtain information about the velocity of blood at a plurality of measuring points;
   means for detecting light reflected from said eye and for storing information about said light,
   means for calculating a velocity of blood at each of said plurality of measuring points of said eye at a predetermined time based on said stored information,
   means for two-dimensionally imaging and displaying a distribution of blood velocities calculated by said calculating means,
   means for detecting a pulse wave of said person to be tested, and
   means for distribution of blood velocities on said blood velocity distribution displaying means, said wave shape displaying means allowing said blood velocity distribution displaying means to display a mark showing a level of said wave shape detected at the predetermined time, said mark being superimposed upon said wave shape.

2. An apparatus according to claim 1, wherein said wave shape displaying means comprises means for predetermining said level of said wave shape.

3. An apparatus according to claim 1, wherein said beam directing means has a movable mirror to select an area of a retina of said eye to be irradiated.

4. An apparatus for imaging and displaying a a velocity of blood in a blood vessel comprising:
   an illuminating optical system for illuminating and observing an eye of a person to be tested,
   a photographing optical system for photographing said eye,
   a measuring optical system for measuring a velocity of blood in said eye by directing a laser beam onto said eye and detecting light reflected from said eye in order to obtain information about a velocity of blood at each of a plurality of measuring points in said eye,
   means for storing said information,
   means for calculating the velocity of blood at each of said plurality of measuring points in said eye at a predetermined time based on said information,
   means for two-dimensionally imaging and displaying velocities of blood calculated by said calculating means,
   pulse wave detecting means for detecting a pulse wave of said person,
   means for controlling said displaying means to display a wave shape of said detected pulse wave together with said velocities on said displaying means, said display controlling means allowing said displaying means to display a mark showing a level of said wave shape detected at said predetermined time, said mark being superimposed upon said wave shape.

5. An apparatus according to claim 4, wherein said measuring optical system has means for selecting an area of said eye to be irradiated and said photographing optical system has a reticule image projecting optical system for imaging and displaying said irradiated area of said eye, said reticule image projecting optical system being moved in response to movement of said selecting means.

* * * * *

UNITED STATES PATENT AND TRADEMARK OFFICE
CERTIFICATE OF CORRECTION

PATENT NO. : 5,240,006
DATED : August 31, 1993
INVENTOR(S) : Hitoshi Fujii et al.

It is certified that error appears in the above-indentified patent and that said Letters Patent is hereby corrected as shown below:

Abstract, line 6, change "are" to --is--.

Abstract, line 10, change "shaped" to --shape--.

Claim 1, column 8, line 33, after "means for", insert --displaying a wave shape of said detected pulse wave together with said--.

Claim 4, column 8, line 46, delete second occurence of "a".

Signed and Sealed this

Fifth Day of July, 1994

BRUCE LEHMAN

*Attest:*

*Attesting Officer*  *Commissioner of Patents and Trademarks*